United States Patent [19]

Uchidomi

[11] Patent Number: 5,268,642
[45] Date of Patent: Dec. 7, 1993

[54] METHOD AND APPARATUS FOR MEASURING ELECTRICAL CONDUCTIVITY OF LIQUID

[75] Inventor: Masato Uchidomi, Yamaguchi, Japan

[73] Assignee: Central Glass Company Limited, Ube, Japan

[21] Appl. No.: 780,206

[22] Filed: Oct. 22, 1991

[30] Foreign Application Priority Data

Oct. 31, 1990 [JP] Japan .................. 2-294891
Nov. 30, 1990 [JP] Japan .................. 2-334182

[51] Int. Cl.$^5$ .................. G01N 27/60; G02B 27/00
[52] U.S. Cl. .................. 324/445; 250/551
[58] Field of Search .................. 324/445; 250/551; 174/11 GF; 336/229, 174; 323/356, 357

[56] References Cited

U.S. PATENT DOCUMENTS

| | | | |
|---|---|---|---|
| 2,038,507 | 4/1936 | Edsall | 114/17 GF |
| 3,054,946 | 8/1962 | Esterson | 324/445 |
| 3,292,077 | 12/1966 | Sloughter | 324/445 |
| 3,510,761 | 5/1970 | Brown . | |
| 3,603,873 | 9/1971 | Cirulis . | |
| 3,772,514 | 11/1973 | Sunderland | 250/551 |
| 3,855,522 | 12/1974 | Kobayashi | 324/445 |
| 3,883,796 | 5/1975 | Holt et al. . | |
| 4,220,920 | 9/1980 | Gross . | |
| 4,446,841 | 5/1984 | Van Siclen, Jr. | 250/551 |
| 4,957,839 | 9/1990 | Rokutanzono et al. . | |
| 5,103,084 | 4/1992 | Williams et al. | 250/551 |

FOREIGN PATENT DOCUMENTS

| | | |
|---|---|---|
| 2325055 | 11/1973 | Fed. Rep. of Germany . |
| 3228020 | 2/1983 | Fed. Rep. of Germany . |
| 54-34632 | 10/1979 | Japan . |
| 62-164120 | 7/1987 | Japan . |
| 0596871 | 3/1978 | U.S.S.R. .................. 324/445 |

OTHER PUBLICATIONS

Bulletin D'Instrumentation Nucleaire; Jan. 1970; pp. 38–41, and English translation.
Soviet Electrochemistry; Mar. 1974; pp. 390–394.
Review of Scientific Instruments; Nov. 1979; pp. 1433–1436.

Primary Examiner—Kenneth A. Wieder
Assistant Examiner—Maura K. Regan
Attorney, Agent, or Firm—Keck, Mahin & Cate

[57] ABSTRACT

To measure the electrical conductivity of a liquid, or the concentration of a solution, an insulated combination of two transformers each of which has an annular core is immersed in the liquid such that the two transformers are electromagnetically coupled by a coil of the liquid which passes through the center holes of the two transformers. By applying AC voltage to the primary winding of the first transformer a current that is proportional to the conductivity of the liquid flows in the liquid coil, and this current is represented by the output of the second transformer. On the second transformer a compensation winding is wound so as to negate magnetic flux produced by the flow of the current in the liquid coil. To adjust a current which is made to flow in the compensation winding so as to render the output of the second transformer null, a photoconductive device such as CdS cell is used in combination with a light-emitting device, and the voltage to drive the light-emitting device is controlled based on the phase and magnitude of the output of the second transformer. The invention includes an improved manner of holding the two transformers in a chamber in a synthetic resin body and preventing corrosion in the case of measuring the conductivity of a corrosive liquid such as hydrofluoric acid solution.

13 Claims, 5 Drawing Sheets

METHOD AND APPARATUS FOR MEASURING ELECTRICAL CONDUCTIVITY OF LIQUID

BACKGROUND OF THE INVENTION

This invention relates to a method and apparatus for measuring the electrical conductivity of a liquid, or the concentration of a solution, by using electromagnetic induction.

It is known to measure the conductivity of a liquid by electromagnetically inducing an AC current in the liquid and measuring that current by converting it into a voltage signal. When the liquid is a solution the concentration of the solution can be determined from the measured conductivity.

As shown, for example, in U.S. Pat. No. 3,603,873 and JP 54-34632 (Utility Model), it is usual to use a pair of transformers, one called excitation transformer and the other called detection transformer, each of which has an annular core. In an insulated state the two transformers are immersed in the liquid such that the secondary side of the excitation transformer is electromagnetically coupled with the primary side of the detection transformer by a looping path or coil of the liquid which passes through the center holes of the two annular transformers. In other words, a liquid coupling coil intersects the two annular transformers. When an AC voltage is applied to the primary winding of the excitation transformer an AC current is induced in the liquid coupling coil, and the intensity of this current is proportional to the conductivity of the liquid.

In principle the current in the liquid and hence the conductivity of the liquid can be measured by measuring an AC voltage across the secondary winding of the detection transformer. Actually, however, the accuracy of measurement by this method is restricted by the magnetic and some other characteristics of the detection transformer core so that an error of about 1% or more is inevitable.

To reduce the influence of the characteristics of the detection transformer on the accuracy of measurement it is possible to employ a null-balance method (auto-balance method). For this method, a compensation winding is wound on the detection transformer core in a direction chosen so as to negate a magnetic flux produced by the flow of a current in the aforementioned liquid coupling coil, and a variable resistor is connected to the compensation coil. Based on an error signal representative of a current that flows in the secondary winding of the detection transformer, a servomotor is driven to vary the resistance of the variable resistor thereby to vary a current flowing in the compensation winding such that the error signal approaches zero. When the error signal reaches zero the current flowing in the liquid coupling coil can be determined by reading the resistance of the variable resistor.

However, this null-balance method has inherent disadvantages. Since the apparatus has mechanically movable parts it is necessary to use a high-output amplifier, and the apparatus becomes costly and relatively short in service life. When the variable resistor is a wire wound resistor having a movable contact in contact with the wound wire it is impossible to really continuously vary the resistance, so that a limit is placed on the resolution of the measuring apparatus. Furthermore, since the wound wire of the resistor constitutes a coil and acts as an inductance element the aforementioned error signal includes a reactive current with a phase delay of 90 degrees, and therefore the null point becomes obscure. For these reasons errors in measurement reach ±3% or more.

Besides, there are some problems about the durability and stability of the sensing part of a conductivity measuring apparatus of the electromagnetic induction type. In conventional apparatus of this type it is usual to confine the two annular transformers in an insulating body which is to be immersed in a liquid to measure the conductivity of the liquid. The body is formed with a cross-sectionally annular chamber in which the two transformers are received in a coaxial and parallel arrangement and has holes to provide the aforementioned liquid coupling coil. The material of the body is selected according to the properties of liquids which are the objects of measurement. Synthetic resins excellent in chemical resistance, such as hard polyvinyl chloride, heat-resistant polyethylene and polytrifluoroethylene are selectively used according to the required degree of heat resistance. A superior material is a copolymer of tetrafluoroethylene and perfluoroalkylvinyl ether (abbriated to PFA) which is excellent in heat resistance and also in moldability and machinability.

However, in the case of measuring the conductivity of a very corrosive liquid such as a hydrofluoric acid solution there is a problem about the durability of the sensor part of the measuring apparatus even though PFA is used as the body material. Although the cross-sectionally annular chamber in the body is airtightly closed the chamber is defined by relatively thin walls, and the highly corrosive vapor of hydrofluoric acid can permeate the relatively thin walls and intrude into the chamber. Therefore, the windings and cores of the two transformers in the chamber and the leads extending from the transformers are gradually corroded, and in about 1 to 3 months the sensing part is liable to exhibit a serious change in its characteristics in most cases by reason of increased contact resistances. In an extreme case the sensing part fails by wire breaking.

Usually the annular cores of the two transformers are made of a magnetically high-permeability alloy and decreasing the iron loss. To secure the annular transformers in the cross-sectionally annular chamber in the body of the sensing part it is usual to make the outer and inner diameters of the transformers such that the respective transformers make tight contact with the radially outer and inner walls of the chamber. However, in our view this manner of securing is not favorable for the stability of the output characteristic of the sensing part.

SUMMARY OF THE INVENTION

It is an object of the present invention to provide an improved method for very accurately measuring the electrical conductivity of a liquid by the electro-magnetic induction method.

It is another object of the invention to provide an apparatus for measuring the electrical conductivity of a liquid by the method according to the invention without using mechanically movable parts.

It is a further object of the invention to provide an improved construction of the sensing part of an apparatus according to the invention to enhance durability and stability.

The present invention provides a method of measuring the electrical conductivity of a liquid, which has the steps of immersing an insulated combination of a first transformer having an annular core, a second transformer having an annular core and a compensation coil which is wound on the core of the second transformer in the liquid such that the secondary side of the first transformer and the primary side of the second transformer are electromagnetically coupled by a coil of the liquid which passes through the center holes of the first and second transformers, applying an AC voltage to the primary winding of the first transformer to cause an induced current to flow in the liquid coil, making a compensation current flow in the compensation winding which is wound in a direction chosen so as to negate magnetic flux produced by the induced current by the flow of the compensation current, producing an AC signal representative of the output of the second transformer on the secondary side thereof, adjusting the compensation current based on that signal such that the signal approaches null and measuring the compensation current when the signal reaches null. The method according to the invention is characterized in that a photoconductive device of which the resistance varies according to the quantity of light incident thereon is connected to the compensation winding such that the compensation current varies as the resistance of the photoconductive device varies, that a light-emitting device is provided so as to emit light toward said photoconductive device and that a voltage to drive the light-emitting device is controlled based on the phase and magnitude of the aforementioned signal.

The conductivity measuring method according to the invention is an autobalancing null-balance method, and the principal feature of the invention is to directly measure a current that flows in the compensation winding by using a combination of a light-emitting device and a photo-conductive device instead of measuring a mechanical displacement as an indication of the current in question. It is suitable to use a combination of a light-emitting diode and a non-polar photoconductive device such as CdS cell, CdSe cell or a photoconductive MOS field-effect transistor (FET).

In a null-balance method in which a compensation current is to be measured it is usual to use a variable resistor. To measure the conductivity K of a liquid arbitrarily chosen from various kinds of liquids ranging from 0 (zero) to $K_{max}$ in conductivity by such a null-balance method it is necessary that the resistance R of the variable resistor is freely adjustable over the range from $\infty$ (infinity) to $R_{min}$ corresponding to $K_{max}$, but conventional variable resistors such as wire wound resistors do not exactly meet this requirement. When, for example, a CdS cell is used as the variable resistor in combination with a light-emitting diode the resistance R of the CdS cell becomes accurately in inverse proportion to the quanity of light emitted by the light-emitting diode, and the resistance is easily variable over the range from $\infty$ to $R_{min}$ which is necessary for measuring conductivities ranging from 0 to $K_{max}$.

A non-polar photoconductive device used in the present invention exhibits a stepless and really continuous change in resistance. Therefore, a conductivity measuring apparatus according to the invention has infinite resolution. The photoconductive device does not produce inductance or capacitance and can be regarded as a pure resistance element, and hence the null point in the null-balance method never becomes obscure. Besides, when an AC voltage is used the photoconductive device is very low in waveform distortion (in the case of CdS cell, waveform distortion is less than 0.006% over the range from 20 Hz to 10 KHz), so that there is little possibility of the intrusion of an error current attributed to distorted waves. In this invention no mechanically movable part is used to vary the resistance of the photoconductive device, and the photoconductive device itself is very small in inertia and makes a high-speed response to a change in the quantity of light incident thereon.

By virtue of the above described matters the conductivity measuring method or apparatus according to the invention is remarkably high in the accuracy of measurement and very good in controllability. By the invention, errors in measurement can be made less than ±0.1%. Besides, an apparatus according to the invention can be produced at relatively low cost.

In another aspect the invention provides an apparatus for measuring the conductivity of a liquid, the apparatus including (A) a sensing part which is to be immersed in the liquid and has an insulated combination of a first transformer having an annular core, a second transformer having an annular core and a compensation winding which is wound on the core of the second transformer, the first and second transformers being arranged such that when an AC voltage is applied to the primary winding of the first transformer while the sensing part is in the liquid the secondary part of the first transformer and the primary part of the second transformer are electromagnetically coupled by a coil of the liquid which passes through the center holes of the first and second transformers so that an induced current flows in the liquid coil, the compensation coil being wound in a direction chosen so as to negate magnetic flux produced by the induced current by making a compensation current flow in the compensation coil, and (B) a detecting part having a current supply means for making the compensation current flow in the compensation coil, a feedback means for producing a signal representative of the output of the second transformer on the secondary side thereof, an adjusting means for adjusting the compensation current based on the aforementioned signal such that the signal approaches null and a detection means for measuring the compensation current when the signal reaches null. The apparatus is characterized in that the adjusting means comprises a light-emitting device, a control means for controlling a voltage to drive the light-emitting device based on the magnitude of the aforementioned signal and the result of comparison of the phase of the signal with a reference phase and a photoconductive device which is connected to the compensation coil and arranged so as to receive light emitted by the light-emitting device, the resistance of the photoconductive device being variable according to the quantity of the light.

In a preferred embodiment of the apparatus according to the invention, the sensing part further comprises a body which is made of an insulating material. The body has an upper end and a lower end and is formed with a cross-sectionally annular chamber which extends from the lower end and terminates at a distance from the upper end, a central hole which extends from the lower end in a region radially inside the inner circumference of the cross-sectionally annular chamber and terminates at a distance from the upper end and at least one through-hole which intersects the central hole without intersecting the aforementioned chamber. The first transformer and the second transformer are in a coaxial and parallel arrangement and confined in the cross-sectionally annular chamber so as to be spaced from the radially outer and inner walls of the chamber.

The body further comprises a closure means for airtightly closing the lower end and is further formed with at least one gas introducing hole which extends from the upside to a bottom region of the cross-sectionally annular chamber without intersecting the aforementioned through-hole(s) for introducing a dry and noncorrosive gas into the chamber and at least one gas discharging hole which extends from a bottom region of the chamber upward to allow the gas to flow out of the chamber.

Thus, the invention proposes to continuously purge corrosive vapor from the cross-sectionally annular chamber in which the annular transformers are placed by circulating a dry and noncorrosive gas such as dry air or nitrogen gas through the chamber. Needless to mention the purpose of purging the corrosive vapor is to prevent corrosion of the transformes and leads and to consequently enhance durability of the sensing part of the apparatus. For this purpose it is effective to keep the annular transformers isolated from the radially outer and inner walls of the chamber so as to provide clearances for the flow of the aforementioned gas.

In securing the annular transformers in the cross-sectionally annular chamber in a plastic body it is necessary to give consideration to the influences of external force on the output characteristics of the transformers. With respect to transformers using annular cores made of permalloy, we have found that the output characteristics are considerably influenced by external force acting in the direction radially of the annular transformers and that, in contrast, the influence of external force acting in the direction axially of the annular transformers is very little. Therefore, the isolation of the annular transformers from the radially outer and inner walls of the chamber is very favorable for stabilization of the output characteristics. According to the invention the two transformers are secured in the chamber by pressing them against the bottom of the chamber in the axial direction. The influence of the pressing load on the output characteristics is tolerable and can be further reduced by confining each transformer in a suitable casing.

The sensitive part of a conductivity measuring apparatus according to the invention is very good in durability and stability even when the object of measurement is a highly corrosive liquid such as a hydrofluoric acid solution.

DESCRIPTION OF THE PREFERRED EMBODIMENTS

Figure 1:
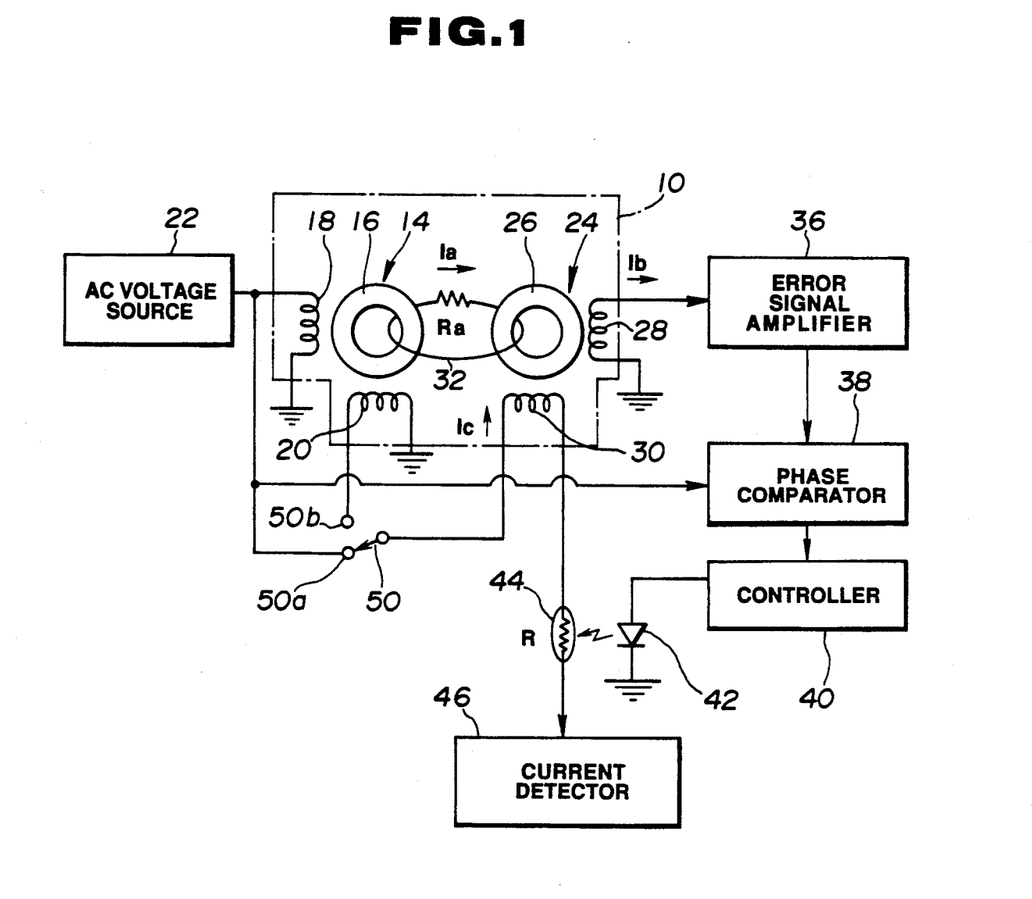
FIG. 1 is a block diagram showing the principle of a conductivity measuring apparatus as an example of the invention.

FIG. 1 illustrates an example of the conductivity measuring apparatus according to the invention. A sensing part 10 of the apparatus includes an excitation transformer 14 having an annular core 16 on which a primary winding 18 and another winding 20 are wound and a detection transformer 24 having an annular core 26 on which a winding 28 and a secondary winding 30 are wound. The primary winding 18 of the transformer 14 is connected to an AC voltage source 22 stable in the amplitude of output, such as a constant-voltage AC oscillator. The two transformers 14 and 24 are confined in a suitably designed body (not shown) of the sensing part 10 at a short distance from each other. Usually the annular cores 16 and 26 of the two transformers are arranged coaxially parallel to each other. The body of the sensing part is formed with apertures such that when the body is immersed in a liquid of which the conductivity is to be measured a looping path of the liquid is formed through the center holes of the two annular cores 16, 26. The looping liquid path constitutes a liquid coupling coil 32 having a resistance $R_a$.

The winding 28 of the detection transformer 24 is wound on the secondary side. The winding 30, which is called compensation winding, is wound such that a current $I_c$ flowing in this winding 30 can negate a magnetic flux produced by the flow of a current $I_a$ in the liquid coupling coil 32.

Besides the sensing part 10 and the AC oscillator 22, the apparatus has a light-emitting device 42, an error signal amplifier 36 to amplify a signal representative of a current $I_b$ flowing in the winding 28 of the detection transformer 24, a phase comparator 38 to which the output of the amplifier 36 and the output of the AC oscillator 22 are inputted, a controller 40 such as an integrator which utilizes the output of the phase comparator 38 and controls a voltage applied to the light-emitting device 42, a photoconductive device 44 which is positioned so as to receive the light emitted from the device 42 and connected to the compensation winding 30 in the sensing part 10, a current detecting circuit 46 to measure the current $I_c$ flowing through the winding 30 and the photoconductive device 44 and a changeover switch 50 to selectively connect the winding 30 to the AC oscillator 22 or to the secondary winding 20 of the excitation transformer 14. These components are placed in a control box (not shown).

It is preferable to use a light-emitting diode as the light-emitting device 42, though it is also possible to use a different device, e.g. a tungsten lamp, which varies the quantity of emitting light in proportion to the magnitude of the applied voltage or current.

The photoconductive device 44 is required to be a nonpolar device of which the resistance continuously varies according to the quantity of light incident thereon. It is preferable to use a CdS cell or a CdSe cell because, in combination with a light-emitting diode, such a photoconductive cell is very low in waveform distortion. It is also possible to use a phototransitor such as a photoconductive MOS FET, though the accuracy of measurement of conductivity somewhat lower because of relatively large distortion of waveform. This example of the invention used a photocoupler in which a light-emitting diode and a CdS cell are integrated.

When the changeover switch 50 selects contact 50a to directly connect the compensation winding 30 to the AC voltage source 22, the operation of the apparatus of FIG. 1 is as follows.

The output voltage of the constant-voltage AC oscillator 22 in E; the number of turns of the winding 18 of the transformer 16 is $N_1$; and the conductance of the sample liquid is K (product of the reciprocal of the resistance $R_a$ of the liquid coupling coil 32 by a cell constant of the sensing part 10). A current $I_a$ that is induced in the liquid coupling coil 32 is given by the following equation. That is, the current $I_a$ is proportional to the conductivity of the sample liquid.

$$I_a = E \cdot K/(\alpha \cdot N_1) \quad (1)$$

where $\alpha$ is the cell constant.

In the compensation winding 30 of which the number of turns is $N_3$, current $I_c$ flows so as to negate the magnetic flux produced by the current $I_a$. The photoconductive cell 44 has a variable resistance R. Therefore, $I_c = E/R$. The resistance R is adjusted so as to render the current $I_c$ equal to $I_a/N_3$ thereby to establish an equilibrium. In the equilibrium state current $I_b$ flows in the secondary winding 28 of the transformer 24 is null, so that the output of the error signal amplifier 36 is null. In this state the current $I_c$ is directly proportional to the conductivity of the sample liquid so that the conductivity can be determined by measuring the current $I_c$ with the detection circuit 46.

If the conductivity of the sample liquid increases, for example, by reason of an increase in the concentration of a solute the detection transformer 24 loses its equilibrium, so that an imbalance current $I_b$ flows in the winding 28. $I_b = (I_a - N_3 \cdot I_c)/N_2$, where $N_2$ is the number of turns of the winding 28. A signal representative of the imbalance current $I_b$ is amplified by the amplifier 36, and the comparator 38 makes phase comparison of the amplified signal with the output of the AC voltage oscillator 22 to provide a positive signal to the controller 40 when the two signals are in-phase and a negative signal in the case of opposite phases. In the apparatus of FIG. 1 the comparator 38 outputs a positive signal which is proportional to the imbalance current $I_b$.

To control a voltage $E_p$ to be applied to the light-emitting device 42 the controller 40 makes an arithmetic operation represented by the following equation at predetermined time intervals.

$$E_p = A/T \int I_b dt + E_{p-1}$$

where A is a coefficient of conversion to voltage, T is the integration time, and $E_{p-1}$ is the result of the last arithmetic operation.

By application of the voltage $E_p$ the light-emitting device 42 emits light the quantity of which is proportional to the magnitude of the voltage $E_p$. The controller 40 repeats the aforementioned arithmetic operation at short time intervals such as, for example, 0.1 sec to replace the lastly computed voltage magnitude $E_{p-1}$ by a newly computed voltage magnitude $E_p$ and output the voltage $E_p$ at each repetition. When the signal representative of the imbalance current $I_b$ and the output of the AC oscillator 22 are in-phase, i.e. in the present example, the value of $A/T \int I_b dt$ is positive, so that the output voltage $E_p$ of the controller 40 gradually increases. In the case of opposite phases the value of $A/T \int I_b dt$ is negative, so that the output voltage $E_p$ gradually decreases.

The light emitted by the light-emitting device 42 is incident on the photoconductive device 44, whereby the resistance R of the photoconductive device 44 varies in inverse proportion to the quantity of light. Therefore, the current $I_c (= E/R)$ flowing in the compensation winding 30 varies toward the equilibrium value $I_a/N_3$, where $I_a$ is proportional to the conductivity of the sample liquid. In this example the quantity of light emitted by the light-emitting device 42 is larger than that in the last equilibrium state, and the resistance R of the photoconductive device 44 decreases in inverse proportion to the quantity of light. Therefore, the compensation current $I_c$ increases when the conductivity of the sample liquid increases. The increase in the current $I_c$ automatically follows the increase in the conductivity until an equilibrium is reached.

With an apparatus of the type shown in FIG. 1, it is possible to measure the concentration of 55% hydrofluoric acid solution with high accuracy less than ±0.1% in error, and as a conductivity sensor the same apparatus is excellent in linearity: deviations are less than ±0.02%.

Figure 2:
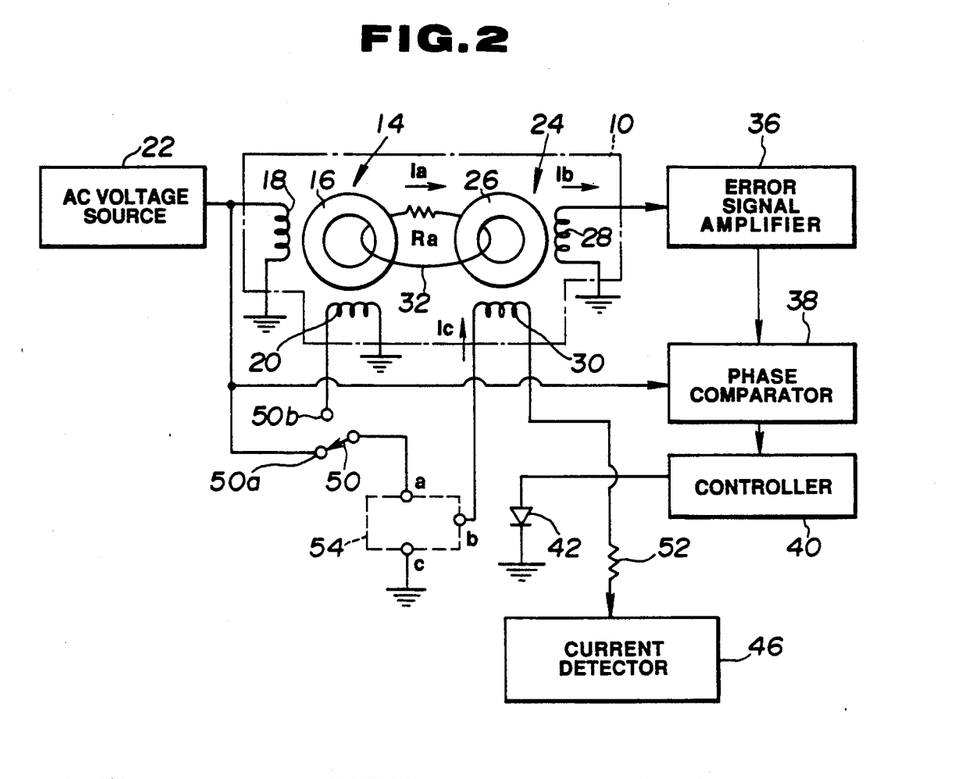
FIG. 2 is a block diagram showing a partial modification of the apparatus of FIG. 1.

FIG. 2 shows another example of apparatus according to the invention. In the apparatus of FIG. 1 the photoconductive device 44 is connected between and in series with the compensation winding 30 and the current detecting circuit 46 in order to directly control the current $I_c$ flowing in the winding 30. In the apparatus of FIG. 2, a current limiting resistance 52 is connected between and in series with the winding 30 and the circuit 46, and a light-sensitive circuit 54 including a photoconductive device is inserted between the coil 30 and the AC voltage source 22. In this case the current $I_c$ is controlled by controlling a voltage applied to the winding 30. The construction of the light-sensitive circuit 54 may be any of three options shown in FIGS. 3, 4 and 5, respectively.

Figure 3:
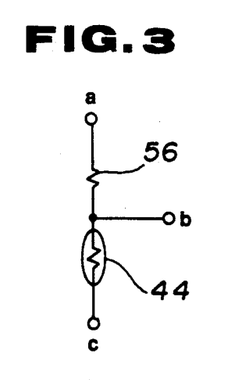
FIGS. 3 to 5 show three options of the light-sensitive circuit in FIG. 2.
Figure 4:
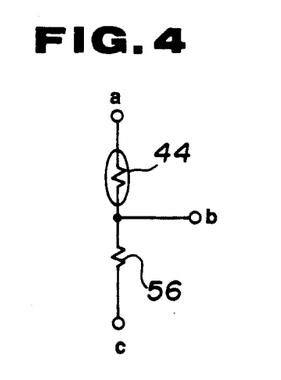
Figure 5:
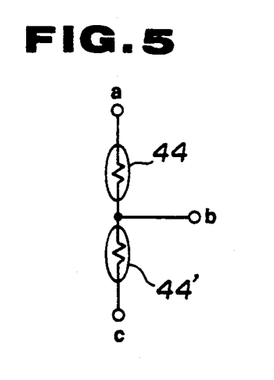

In the circuit 54 of FIG. 3, the photoconductive device 44 and a fixed resistance 56 constitute a voltage divider. The circuit 54 of FIG. 4 is analogous to that of FIG. 3 except the reversed arrangement of the photoconductive device 44 and the resistance 56. The arrangement of FIG. 4 is rather advantageous over that of FIG. 3 because in the case of FIG. 3 the lower boundary of the range of measurable conductivities becomes higher since the minimum resistance of the photoconductive device 44 cannot arbitrarily be reduced. However, even when the arrangement of FIG. 3 is employed the apparatus of FIG. 2 is superior to conventional conductivity sensors of the electromagnetic induction type. The circuit 54 of FIG. 5 has a second photoconductive device 44' in place of the fixed resistance 56 in FIG. 4. In the case of employing the circuit 54 of FIG. 5 the apparatus of FIG. 2 is supplemented with another light-emitting device (not shown) in combination with the second photoconductive device 44', and an arithmetic unit (not shown) is connected to the controller 40 in order to operate the additional light-emitting device by computing the difference between the maximum of the control current ($P_{max}$) for the light-emitting device and the output current (P) of the control circuit, $P_{max} - P$. In this case the resistance R' of the second photoconductive device 44' is varied inversely to the resistance R of the first photoconductive device 44.

As to the changeover switch 50 in the apparatus of FIG. 1 or FIG. 2, usually it is preferable to select the contact 50a to directly use the AC oscillator 22 as the voltage source for the compensation winding 30, though it is also possible to select the contact 50b to use the winding 20 of the excitation transformer 14 as the voltage source. If a separate AC oscillator (not shown) is employed as the voltage source for the compensation winding 30 the winding 20 and the changeover switch 50 can be omitted.

As the phase comparator 38 it is possible to use an ordinary phase comparator, and it is also possible to use a different device such as a multiplier.

The controller 40 may be of any type insofar as it is capable of producing a signal for controlling the drive current of the light-emitting device 42 based on the magnitude and phase of the signal representative of the imbalance current $I_b$ and adjusting the level of the output current according to the response speed and some other characteristics of the light-emitting device 42 and the photoconductive device 44. For example, an integrator or PID controller or a microcomputer can be used.

As mentioned hereinbefore the present invention includes improvements in the mechanical construction of the sensing part 10 of the conductivity measuring apparatus. In this respect FIGS. 6–9 show a preferred embodiment of the invention.

Figure 6:
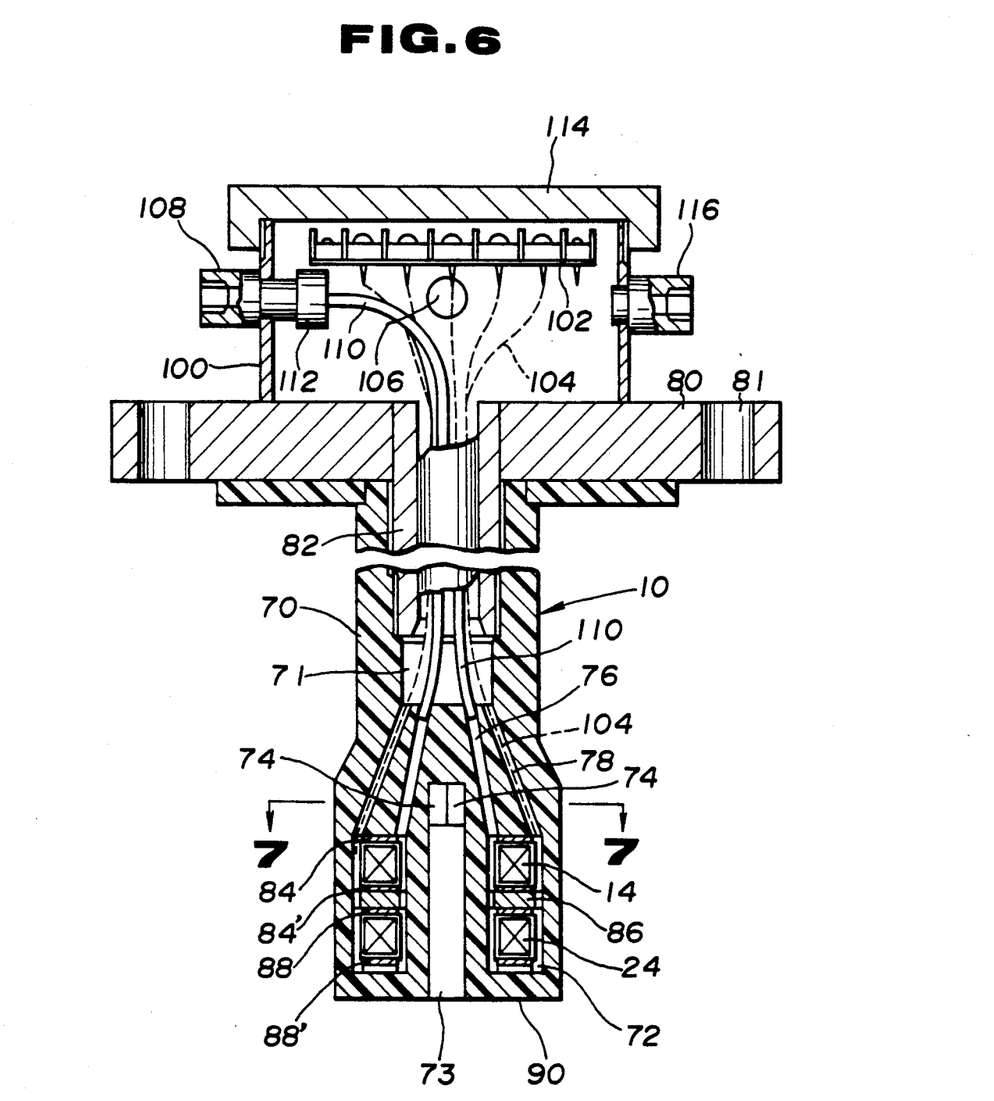
FIG. 6 is a partially cutaway, longitudinal sectional view of a preferred embodiment of the sensing part of a conductivity measuring apparatus according to the invention.

The sensing part 10 has a generally cylindrical body 70 which is made of an insulating material such as, for example, PFA. From one end of the body 70 an axial center hole 71 extends in a relatively long portion of the body and terminates at some distance from the opposite end, and a screw thread is formed on the inner cylindrical surface defining the hole 71. To fix the body 70 to a flange 80 having a through-hole in the center, a support pipe 82 formed with a screw thread on the outer surface is fitted into the through-hole of the flange 80 and fixed by welding, and the body 70 is screwed on the support pipe 82. The flange 80 has bolt holes 81 for attachment to a liquid container. Usually the flange 80 and the support pipe 82 are made of stainless steel. From the opposite end the body 70 is formed with a cross-sectionally annular hole 72 and an axial center hole 73. The holes 72 and 73 terminate at a distance from the bottom of the aforementioned hole 71. That is, the body 70 is in the shape of a double tube only in an end portion remote from the flange 80, and there is a solid portion between this end portion and the opposite portion formed with the center hole 71.

Figure 7:
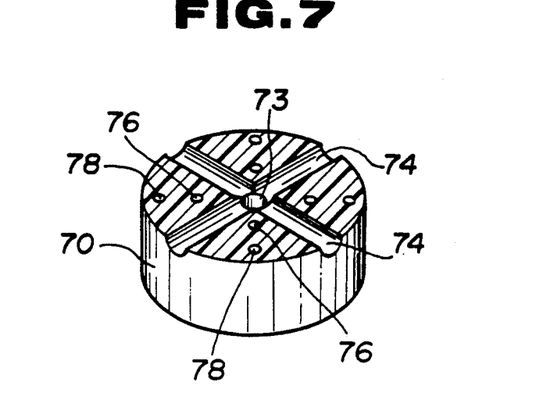
FIG. 7 is a fragmentary illustration showing a section taken along the line 7—7 in FIG. 6.

As can be seen in the sectional view in FIG. 7, two radial through-holes 74 are formed in the solid portion of the body 70 so as to cross each other and perpendicularly intersect the bottom portion of the axial center hole 73. Besides, a plurality of gas introducing holes 76 and a plurality of gas discharging holes 78 extend through the solid portion of the body 70 from the bottom of the hole 71 to the bottom of the cross-sectionally annular hole 72. Both the holes 76 and the holes 78 are distributed over the cross sections of the body so as to pass through each of the four sectors divided by the two crossing through-holes 74. In this embodiment the gas introducing holes 76 are at relatively short distances from the center axis of the body 70, whereas the gas discharging holes 78 are at relatively short distances from the radially outer surface of the body 70.

Figure 8:
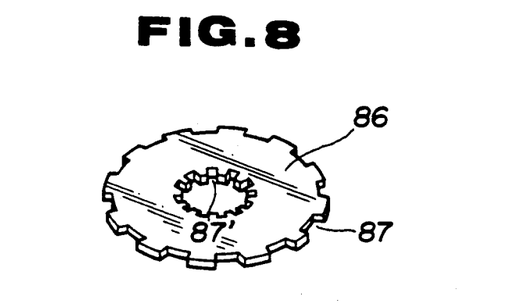
FIG. 8 is a perspective view of a reinforcing ring used in the sensing part of FIG. 6.

The cross-sectionally annular hole 72 of the body 70 receives the annular excitation transformer 14 and the annular detection transformer 24 in a coaxial and parallel arrangement. The two transformers 14, 24 are approximately similar in outer and inner diameters, and the annular hole 72 allows a clearance of about 1-2 mm between the radially outer side of each transformer 14, 24 and the outer cylindrical wall of the hole 72 and a similar clearance between the radially inner side of each transformer 14, 24 and the inner cylindrical wall of the hole 72. The excitation transformer 14 is sandwiched between two annular packings 84, 84', and the detection transformer 24 is sandwiched between two annular packings 88, 88'. These packings are made of an elastic material such as a fluorine rubber. Besides, a reinforcing ring 86 is interposed between the two transformers 14 and 24. As shown in FIG. 8 the reinforcing ring 86 has a plurality of cuts in the radially outer edge so as to form superficial gear teeth of a gear wheel and a plurality of cuts 87' in the radially inner edge so as to form superficial gear teeth. The outer and inner diameters of the reinforcing ring 86 are such that the ring 86 slidably fits in the cross-sectionally annular hole 72. Alternative to the illustrated cuts 87 and 87', the reinforcing ring 86 may be formed with a plurality of through-holes (not shown) in radially outer and inner peripheral regions.

Figure 9:
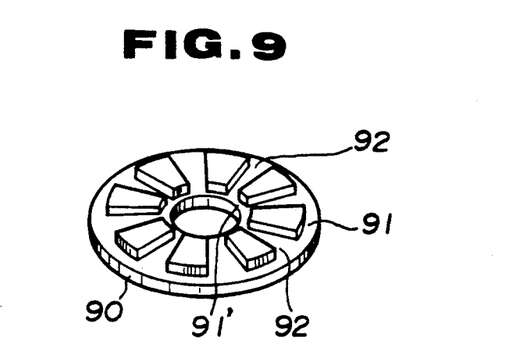
FIG. 9 is a perspective view of a lid member used in the sensing part of FIG. 6.

At the end of the body 70 the cross-sectionally annular hole 72 is closed by a ring-like retaining lid 90, which is airtightly and forcibly fitted into the hole 72 in order to apply a load on the transformers 14 and 24 in the axial direction. As shown in FIG. 9 the inside surface of the lid 90 is formed with annular grooves 91 and 91' around the radially outer and inner circumferences and a plurality of radial grooves 92 connecting the two annular grooves 91 and 91'. It is optional to form radial through-holes (not shown) connecting the two annular grooves 91, 91' as an alternative to the grooves 92.

Usually the annular cores of the transformers 14, 24 are made of permalloy. For the windings of the transformers it is preferable to use a wire covered with a fluororesin for the purpose of enhancing corrosion resistance.

A connector box 100 is fixed to the top surface of the flange 80. A terminal board 102 is fixed to the inside of the box 100, and leads 104 which extend from the transformers 14 and 24 in the body 70 through some of the gas discharging holes 78 and the support pipe 82 are soldered to the terminals of the board 102. Preferably the leads 104 are sufficiently thick wires covered with a fluororesin. Through a hole 106 in the box 100, cables (not shown) extend from the terminal board 102 to an AC voltage source and the control and detection components shown in FIG. 1 or FIG. 2.

A socket 108 is fitted in the side wall of the box 100, and the socket 108 is connected to a source of dry air or nitrogen gas by a pipe (not shown). In the box 100 a plurality of tubes 110 are connected to the socket 108 by using packings (not shown) and a cap nut 112. The tubes 110 extend into the body 70 through the support pipe 82 and respectively enter the gas introducing holes 76 of the boty 70. Another socket 116 is fitted in the side wall of the box 100, and a pipe (not shown) extends from this socket 116 to a gas cleaning apparatus (not shown). The box 100 has a lid 114.

In measuring the conductivity of a liquid the body 70 of the sensing part 10 is immersed in the liquid. Then the center hole 73 and the two crossing through-holes 74 are filled with the liquid. Since each of the through-holes 74 joins the center hole 73, there is produced a looping path of the liquid which passes through the center holes of the two annular transformers 14, 24 in the parallel arrangement. The looping path of the liquid corresponds to the liquid coupling coil 32 in FIG. 1.

While the body 70 is immersed in the liquid, dry air having a dew point of about −50° C. (by way of example) is continuously introduced into the cross-sectionally annular hole 72 in the body 70 through the tubes 110 extending from the socket 108 and the gas introducing holes 76. For example, the feed rate of dry air is several liters per minute. In the hole 72 the dry air flows through the clearance between each transformer 14, 24 and the radially inner wall of the hole 72 and the cuts 87′ in the radially inner edge of the reinforcing ring 86. At the end of the hole 72 the grooves 91′, 92, 91 of the lid 90 allow the dry air to enter the clearance between the transformer 24 and the radially outer wall of the hole 72. The dry air continues to flow through the cuts 87 in the radially outer edge of the ring 86 and the clearance between the transformer 14 and the radially outer wall of the hole 72 and into the box 100 through the gas discharging holes 78 in the body 70. When the liquid is a highly corrosive liquid such as a hydrofluoric acid solution there is a possibility that a corrosive vapor enters the hole 72 in the body 70 by peameating the lid 90 or the relatively thin wall of the body 70 in the portion formed with the hole 72, but the corrosive vapor is diluted and carried away by the dry air flowing through the hole 72. Therefore, a dry and clean environment can be maintained around the transformers 14, 24, so that the transformers are prevented from corrosing. The air containing the corrosive vapor is discharged from the box 100 by the socket 116 and passed to a cleaning apparatus for neutralization and/or absorption of the corrosive substance.

In the body 70 the reinforcing ring 86, which is in contact with the radially outer and inner walls of the cross-sectionally annular hole 72, serves the purpose of preventing the relatively thin walls of the body 70 in the portion formed with the hole 72 from being deformed by the static pressure of the liquid. That is, the reinforcing ring 86 stabilizes the shape and dimensions of the most important portion of the body 70 and hence stabilizes the cell constant of the sensing part 10. If the temperature of the liquid changes, thermal expansion or shrinkage of the body 70 develops external force which might act on the transformers 14, 24. However, in the direction axially of the transformers 14, 24 the external force is absorbed by the elastic packings 84, 84′, 88, 88′, and in the radial directions the external force does not act on the transformers 14, 24, since sufficient clearances are provided between each transformer and the walls of the hole 72. Therefore, the cores of the transformers 14, 24 are hardly deformed or distorted by external force, and hence the current induced in the secondary winding of the detection transformer 24 are stable unless the conductivity of the liquid varies.

To further stabilize the transformers 14, 24 against external force, it is preferable to confine the core of each transformer (with windings thereon) in a casing formed of a suitable resin such as a phenolformaldehyde resin together with a buffering material such as silicone grease. In this regard, an experiment was conducted in the following way.

Figure 10:
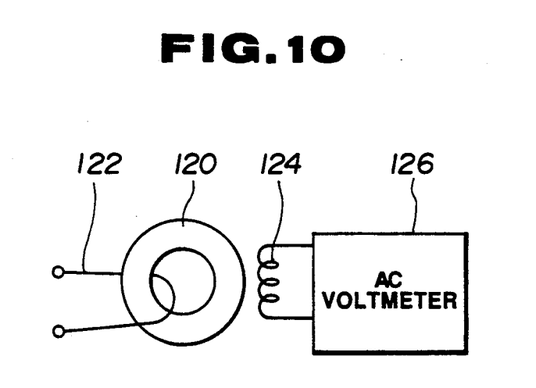
FIG. 10 is a diagram for explanation of a load test on a transformer core for use in the invention.

Referring to FIG. 10, an annular core 120 having an outer diameter of 35 mm, inner diameter of 25 mm and thickness of 5 mm was formed by using a permalloy sheet having a thickness of 25 μm, and an excitation winding 122 of one turn was wound on the core 120. A detection winding 124 was wound on the core 120 and connected to an AC voltmeter 126 to measure the voltage between the two terminals of the winding 124 while a predetermined AC current is flowing in the excitation winding 122. The magnetomotive force was 3 mAT. Before testing, some samples of the core 120 were each confined in a phenol resin casing 38 mm in outer diameter, 22 mm in inner diameter and 8.2 mm in thickness by using a silicone grease as a buffering material.

Figure 11:
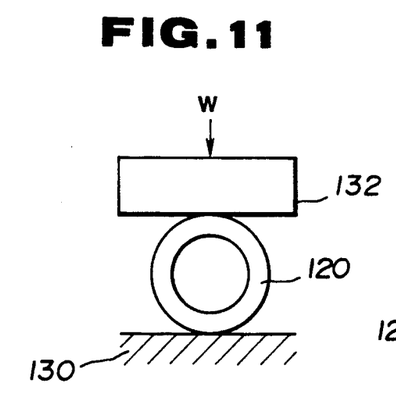
FIGS. 11 and 12 show two different manners of applying a load to the transformer core in FIG. 10.
Figure 12:
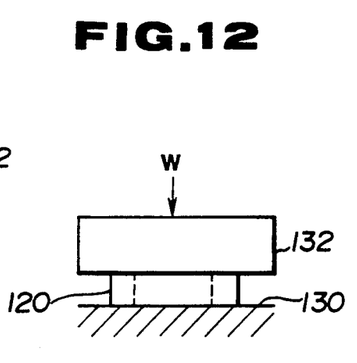

First the measurement was made without applying any load to the core 120. Next, the same measurement was made while a load was applied to the core 120 in the radial direction or in the axial direction. That is, in one case the core 120 was set upright on a platform 130 as shown in FIG. 11, and in another case the core 120 was placed flat on the platform 130 as shown in FIG. 12. In both cases an insulating block 132 was placed on the core 120, and a weight W of 700 g was placed on the insulating block 132.

The influence of the load W on the core 120 was evaluated by measuring a change in the output voltage of the detection winding 124. The degree of the output change, D, was determined by the following equation.

$$D = (V_0 - V_1)/V \times 100 \ (\pm \%)$$

where $V_0$ is the output voltage without load, and $V_1$ is the output voltage under the load W (700 g).

The results are shown in the following table, wherein the subscript "r" to D means the application of the load radially of the core 120 (FIG. 11), and the subscript "a" means the application of the load axially of the core (FIG. 12).

|  | $D_r$ (%) | $D_a$ (%) | $D_r/D_a$ |
| --- | --- | --- | --- |
| without casing | −29.8 | −2.5 | 11.9 |
| with casing | −0.35 | +0.15 | 2.33 |

The above experimental results indicate that the influence of a load in the direction axially of the core on the output of the core is far less than the influence of a load of the same magnitude on the direction radially of the core, and that when the core is confined in a suitable casing the output of the core becomes very stable even though a load is applied in the radial direction.

What is claimed is:

1. In an apparatus for measuring the electrical conductivity of a liquid, the apparatus including (A) a sensing part which is to be immersed in the liquid and has an insulated combination of a first transformer having an annular core, a second transformer having an annular core and a compensation winding which is wound on the core of the second transformer, the first and second transformers being arranged such that when an AC voltage is applied to the primary winding of the first transformer while the sending part is in the liquid the secondary part of the first transformer and the primary part of the second transformer are electromagnetically coupled by a coil of the liquid which passes through the center holes of the first and second transformers so that an induced current flows in the liquid coil, said compensation coil being wound in a direction chosen so as to negate magnetic flux produced by said induced current by making a compensation current flow in the compensation coil, and (B) a detecting part having a current supply means for making said compensation current flow in said compensation coil, a feedback means for producing a signal representative of the output of the second transformer on the secondary side thereof, an adjusting means for adjusting said compensation current based on said signal such that said signal approaches null and a detection means for determining said compensation current when said signal reaches null, the improvement comprising:

said adjusting means comprising a light-emitting device, a control means for controlling a voltage to drive said light-emitting device based on the magnitude of said signal and the result of comparison of the phase of said signal with a reference phase and a photoconductive device which is connected to said compensation coil and arranged so as to receive light emitted by said light-emitting device, the resistance of the photoconductive device being variable according to the quantity of said light, wherein said sensing part further comprises a body which is made of an insulating material and has an upper end and a lower end, said body being formed with a cross-sectionally annular chamber which extends from said lower end and terminates at a distance from said upper end, a central hole which extends from said lower end in a region radially inside the inner circumference of said cross-sectionally annular chamber and terminates at a distance from said upper end and at least one through-hole which intersects said central hole without intersecting said chamber, said first transformer and said second transformer being in a coaxial and parallel arrangement and confined in said chamber so as to be spaced from the radially outer and inner walls of said chamber, said body comprising a closure means for airtightly closing said lower end and being further formed with at least one gas introducing hole which extends from the upside to a bottom region of said chamber without intersecting said at least one through-hole for introducing a dry and noncorrosive gas into said chamber and at least one gas discharging hole which extends from a bottom region of said chamber upward to allow said gas to flow out of said chamber.

2. An apparatus according to claim 1, wherein said sensing part further comprises a reinforcing ring which is inserted between said first and second transformers in said chamber such that the radially outer and inner edges of the reinforcing ring make contact with the radially outer and inner walls of said chamber, respectively, the reinforcing ring being formed with a plurality of openings in a radially outer peripheral region and a radially outer inner peripheral region.

3. An apparatus according to claim 2, wherein said plurality of openings of said reinforcing ring are a plurality of cuts in the radially outer and inner edges of the ring.

4. An apparatus according to claim 2, wherein each of said plurality of openings of said reinforcing ring is a through-hole.

5. An apparatus according to claim 2, wherein said closure means comprises an annular lid which makes tight contact with the radially outer and inner walls of said chamber, said lid being formed with a first annular groove in a radially outer peripheral region of the inside surface, a second annular groove in a radially inner peripheral region of the inside surface and a plurality of radial grooves or holes connecting said first annular groove to said second annular groove.

6. An apparatus according to claim 5, wherein said sensing part further comprises a plurality of elastic and annular packings which are placed in said chamber for cushioning said first and second transformers, said lid being forced into said chamber so as to press said first and second transformers in the axial direction against the bottom of said chamber.

7. An apparatus according to claim 2, wherein the annular cores of said first and second transformers are made of permalloy.

8. An apparatus according to claim 1, wherein said body is made of a copolymer of tetrafluoroethylene and a perfluoroalkylvinyl ether.

9. An apparatus according to claim 1, wherein said light-emitting device is a light-emitting diode.

10. An apparatus according to claim 1, wherein said photoconductive device is a CdS cell.

11. An apparatus according to claim 1, wherein said photoconductive device is a CdSe cell.

12. An apparatus according to claim 1, wherein said control means comprises an integrator.

13. An apparatus according to claim 1, wherein said reference phase is the phase of the AC voltage applied to the primary winding of said first transformer.

* * * * *